(12) United States Patent
Huff et al.

(10) Patent No.: US 7,910,569 B2
(45) Date of Patent: Mar. 22, 2011

(54) MICROBICIDAL COMPOSITIONS AND THEIR USE

(75) Inventors: Jürgen Huff, Ludwigshafen (DE); Shoaib Qureshi, Nottinghamshire (GB); Darren Hodgkinson, Nottingham (GB); Craig Nicklin, Nottingham (GB); Reimer Göttsche, Baden-Baden (DE); Helga Göttsche, legal representative, Baden-Baden (DE); Wendelin Hettler, Sinzheim (DE); David Vincent Roper, Nottingham (GB)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 12/413,059

(22) Filed: Mar. 27, 2009

(65) Prior Publication Data

US 2009/0186860 A1 Jul. 23, 2009

Related U.S. Application Data

(62) Division of application No. 10/578,824, filed as application No. PCT/EP2004/011024 on Oct. 2, 2004, now abandoned.

(30) Foreign Application Priority Data

Nov. 11, 2003 (GB) .................................. 0326284.7

(51) Int. Cl.
*A01N 33/26* (2006.01)
(52) U.S. Cl. ....................................................... 514/150
(58) Field of Classification Search ........................ None
See application file for complete search history.

(56) References Cited

U.S. PATENT DOCUMENTS

| 2,954,314 | A | | 9/1960 | Metzger et al. |
| 4,761,179 | A | * | 8/1988 | Goettsche et al. .......... 106/18.32 |
| 4,857,322 | A | | 8/1989 | Goettsche et al. |
| 5,045,104 | A | * | 9/1991 | McCoy ........................ 504/140 |
| 5,200,421 | A | | 4/1993 | Ludwig et al. |
| 5,332,765 | A | | 7/1994 | Lorentzen et al. |
| 6,261,581 | B1 | | 7/2001 | Gebhardt et al. |
| 2005/0070509 | A1 | | 3/2005 | Zeller et al. |

FOREIGN PATENT DOCUMENTS

| DE | 1 024 743 | 2/1958 |
| DE | 36 05 008 | 8/1987 |
| EP | 0 358 072 | 3/1990 |
| WO | WO-97/32477 | 9/1997 |
| WO | WO-02/098430 | 12/2002 |
| WO | WO-2004/030458 | 4/2004 |

OTHER PUBLICATIONS

Eagleson (Concise Encyclopedia Chemistry, p. 113, 1993).*
HKTDC ("Wood treated with arsenic preservatives face new EU-wide ban", published Jun. 5, 2003).*
Casebolt D., "Boron Wood Preservatives and Their Application to Historic Wooden Vessels at San Francisco Maritime N.H.P.", San Francisco Maritime National Park Association, Jul. 1997.

* cited by examiner

*Primary Examiner* — Brandon J Fetterolf
*Assistant Examiner* — Craig Ricci
(74) *Attorney, Agent, or Firm* — Connolly Bove Lodge & Hutz, LLP

(57) ABSTRACT

A composition comprising a copper salt of N'-hydroxy-N-cyclohexyldiazenium oxide (CuHDO) and a diluent is useful for combating and/or killing bacteria, mould, yeast and algae in industrial materials and or industrial processes. In a preferred embodiment CuHDO is generated in-situ within the application or medium. The composition may additionally include at least one of certain other biocidal active components.

8 Claims, No Drawings

MICROBICIDAL COMPOSITIONS AND THEIR USE

This invention relates to microbicidal compositions and their use. Harmful microorganisms cause damage to many materials, products and manufacturing processes. New microbicidal compositions for preventing this are needed, especially compositions which are effective at high pH values, i.e. at pH values above 4, and especially from 8 to 12.

Many microbicidal compositions for combating microorganisms are commercially available. For example, microbicides known to be effective at high pH values are quaternary ammonium compounds such as cetyl pyridium chloride, di-N-decyl-dimethylammonium chloride or N-hexadecyl-N,N-trimethylammonium bromide. However, these compounds generate foam and are difficult to handle. Other microbicides exist but are not stable at alkaline pH's, especially around and above 10 and hence are not active, one example being the isothiazolone family.

For many years, it has been known (e.g. disclosed by DE-A 10 24 743) that metal salts, such as Ca-, Ba-, Al-, Pb-, Ag-, Cu-, Fe-, Ni-, or Zn-salts of N-alkyl-N-nitrohydroxylamines (also referred to as N'-hydroxy-N-alkyl diazenium oxides) are effective for inhibiting fungal growth.

DE-A 36 05 008 and DE-A 36 39 063 disclose the use of the Cu-salt of N'-hydroxy-N-cyclohexyldiazenium oxide (CuHDO) for the protection of wood.

EP-A 358 072 discloses a method of controlling organisms which grow under moist conditions, such as algae and lichen, by treatment with certain metal salts, notably copper, aluminum or tin salts, or amine salts of N'-hydroxy-N-cyclohexyldiazenium oxide. The biocidal active component may be incorporated directly into a polymer matrix, such as a polymer foil, or may be added to aqueous or organic solvent based media to be protected, such as paints, especially antifouling paints. EP-A 358 072 also discloses to use mixtures of said biocidal components together with other biocides, however, no specific examples are disclosed.

All of the above documents are concerned with controlling, i.e. preventing the growth of, microorganisms.

We have found surprisingly that bacteria, mould, yeast and algae can be killed by the application there of, specifically, the copper salt of N'-hydroxy-N-cyclohexyl-diazenium oxide (CuHDO).

More surprisingly we found the CuHDO prepared in-situ i.e. within the application exhibits an improved effect as compared to pre-prepared CuHDO.

We also found surprisingly that a mixture of CuHDO with any of a wide range of other biocides may exhibit an improved effect against a broad spectrum of microorganisms.

According to a first aspect, the invention provides the use, for combating and/or killing bacteria, yeast/mould and algae in industrial materials and/or industrial processes and manufacturing, of a composition comprising CuHDO salt and a diluent.

According to a second aspect, the invention provides the use, for combating microorganisms of a composition comprising (A) CuHDO and (B) another additional microbicidally active component selected from a range of compounds given below. Such use may result in the killing of the microorganisms.

The CuHDO used in course of the present invention may be pre-prepared as known in the art, i.e. prepared, stored, and used later.

In a preferred embodiment of the invention, the CuHDO used is in-situ, formed using a water-soluble salt of N'-hydroxy-N-cyclohexyldiazenium oxide and a Cu-containing salt, i.e. the active component is generated directly within the application For the case CuHDO is used together with another microbicidal component (B) the range of compounds from which component (B) is selected is as follows:
1. Alcohols, including halogenated alcohols.
2. Isothiazolones.
3. Activated halogen compounds.
4. Formaldehyde release compounds.
5. Phenolic compounds.
6. Aldehydes.
7. Acids and esters.
8. Biphenyls.
9. Urea derivatives.
10. O-acetals, O-formals.
11. N-acetals, N-formals.
12. Benzamidines.
13. Phthalimides.
14. Pyridine derivatives.
15. Quaternary ammonium and phosphonium compounds.
16. Amines.
17. Amphoteric compounds.
18. Dithiocarbamates.
19. Compounds containing active oxygen such as peroxide.
20. Inorganic salts such as metal oxides.

Such compounds may be present, as component (B), either alone or as a mixture of any of these compounds.

Examples of alcohol compounds which may serve as the microbicidally effective component (B) are 2-bromo-2-nitropropane-1,3-diol and 2-(hydroxymethyl)-2-nitro-1,3-propanediol. Examples of isothiazolone compounds are 5-chloro-2-methyl-2H-isothiazol-3-one (CIT), 2-methyl-2H-isothiazol-3-one (MIT), 1,2-benzisothiazol-3(2H)-one, 2-n-octyl-2H-isothiazol-3-one, 4,5-dichloro-2-octyl-2H-isothiazol-3-one and 2-butyl-benzo-[d]isothiazol-3-one and mixtures thereof with one another, including a mixture of CIT with MIT or mixtures of CIT or MIT with any of 1,2-benzoisothiazol-3(2H)-one, 2-octyl-2H-isothiazol-3-one, 4,5-dichloro-2-octyl-2H-isothiazol-3-one and 2-butyl-benzo[d]isothiazol-3-one. Examples of other compounds are dibromodicyanobutane, β-bromo-β-nitrostyrene, 7a-ethyldihydro-1H,3H,5H-oxazolo[3,4-c]oxazole, tetrahydro-1,3,4,6-tetrakis(hydroxymethyl)-imidazo[4,5-d]imidazole-2,5 (1H,3H)-dione, 1,3-dimethyl-5,5-dimethylhydantoin, diazolidinyl ureas and imidazolidinyl ureas, N'-(3,4-dichlorophenyl)-N,N-dimethyl urea, 3,3'-methylenebis(5-methyl-oxazolidine), 2-sodiumsulfidopyridine-N-oxide and its metal salts, dibromonitritopropionamide, tetrakishydroxymethylphosphonium salts, ortho-phenylphenol and salts of ortho-phenylphenol, 1-(3-chloroallyl)-3,5,7-triaza-1-azodiadamantane salts, (5-chloro-2,4-dichlorophenoxy)phenol, 3,4,4'-trichlorocarbanilide (triclocarban), o-benzo-p-chlorophenol, p-hydroxybenzoates, 2-(thiocyanomethylthio) benzothiazole, 3,5-dimethyl-1,3,5-thiadiazinane-2-thione, 2,4-dichlorobenzyl alcohol, chlorothalonil, methylenebis (thiocyanate), peracetic acid, 4,4-dimethyl-oxazolidine, phenoxyethanol, phenoxypropanol, 2,6-dimethyl-m-dioxan-4-ol-acetate, glutaraldehyde, glyoxal, ortho-phthalaldehyde, 4-(2-nitrobutyl)-morpholine, triazines such as 1,3,5-tris-(2-hydroxyethyl)-1,3,5-hexahydrotriazine, quaternary ammonium compounds such as benzalkoniumchloride, polyhexamethylenebiguanide salts, poly(oxyethylene (dimethylimino)ethylene(dimethylimino)-ethylene dichloride, chlorhexidine gluconate, chloroisocyanurates, halogenated hydantoins such as 1-bromo-3-chloro-5,5-dimethylhydantoin and polamines such as polyvinylamine- and polyethylene imine derivatives. Further examples include IPBC, terbutryn, ziram, zineb, dichlofluanid, trichlofuanid, folpet, metal dihexa-2,4-dienoate, tebuconazole, 3-benzo(b)thien-2-yl-5,6-dihydro-1,4,2-oxathiazine, 4-oxide, pyrithiones, thiram, cybutryne, MBT, carbendazim, diuron, chlorotoluron, fluorometuron, thiabendazole, metazachlor, CuSCN, or dicopper oxide.

Preferred components (B) are 2-bromo-2-nitropropane-1,3-diol, 2-methyl-2H-isothiazol-3-one, 1,2-benzisothiazol-3(2H)-one, 2-n-octyl-2H-isothiazol-3-one, a mixture of 5-chloro-2-methyl-2H-isothiazol-3-one with 2-methyl-2H-isothiazol-3-one, dibromodicyanobutane, tetrahydro-1,3,4,6-tetrakis(hydroxymethyl)-imidazo[4,5-d]imidazole-2,5(1H,3H)-dione, 3,3'-methylenebis(5-methyl-oxazolidine), 1,3-dimethyl-5,5-dimethylhydantoin, tetrakishydroxymethylphosphonium salts, ortho-phenylphenol and salts of ortho-phenylphenol, 1-(3-chloroallyl)-3,5,7-triaza-1-azodiadamantane salts, (5-chloro-2,4-dichlorophenoxy)phenol, 3,4,4'-trichlorocarbanilide (triclocarban), p-hydroxy-benzoates, 2-(thiocyanomethylthio) benzothiazole, 3,5-dimethyl-1,3,5-thiadiazinane-2-thione), iodo-2-propynylbutylcarbamate, 2-sodiumsulfidopyridine-N-oxide and its metal salts, 2,4-dichlorobenzyl alcohol, chlorothalonil, methylenebis(thiocyanate), phenoxyethanol, phenoxypropanol, triazines such as 1,3,5-tris-(2-hydroxyethyl)-1,3,5-hexahydrotriazine, quaternary ammonium compounds such as benzalkoniumchloride, polyhexamethylene biguanide salts, poly(oxyethylene(dimethyimino)ethylene (dimethylimino)ethylene dichloride, chlorhexidine gluconate, chloroisocyanurates and polyvinylamines, especially the polyamines disclosed in WO-A-97/32477.

Surprisingly it was found that CuHDO is especially suitable when applied in combination with 2-bromo-2-nitropropane-1,3-diol, 1,2-benzisothiazol-3(2H)-one, 1,3,5-tris-(2-hydroxyethyl)-1,3,5-hexahydrotriazine, 5-chloro-2-methyl-2H-isothiazol-3-one, 2-methyl-2H-isothiazol-3-one, tetrahydro-1,3,4,6-tetrakis(hydroxymethyl)-imidazo[4,5-d]imidazole-2,5(2H,3H)-dione, 1,3-dimethyl-5,5-dimethylhydantoin and polyvinylamines, especially a polyamine containing from 80-100%, more preferably 90-98 wt %, vinylamine units and from 0 to 20 wt % more preferably, 2-10 wt %, vinyl formamide units.

Most preferably, the component used in combination with CuHDO is stable at high pH values.

As mentioned above, CuHDO, even as the sole microbicidal active component, can be used not only to combat the growth of microorganisms, including viruses but also to kill certain microorganisms, especially fungi, more specifically *Aspergillus niger* and *Chaetomium globosum*, and indeed yeasts, e.g. *Saccharomyces cerevisiae*, *Candida albicans* and *Malassezia furfur*, the yeast which causes dandruff, and certain organisms such as *Pseudomonas fluorescens*, *Pseudomonas aeruginosa*, *Alcaligenes faecalis*, *Staphylococcus aureus*, *Staphylococcus epidermis*, *Corynebacterium xerosis*, *Propionibacterium acnes*, *Pityrosporum ovale*, *Aspergillus niger*, *Alternaria alternata*, *Aspergillus versicolor*, *Aureobasidium pullulans*, *Cladosporium cladosporioides*, *Penicillium purpurogenum*, *Phoma violacea*, *Rhodotorula rubra*, *Sporobolomyces roseus*, *Stachybotrys chartarum*, *Ulocladium atrum*, *Chlorella sp*, *Pleurococcus sp*, *Nostoc muscorum*, *Oscillatoria tenuis*, *Stichococcus bacillaris*, and *Trentepohlia aurea*.

Indeed, we found surprisingly that CuHDO had a much stronger effect against fungi and algae than had been previously appreciated and is active against a broader spectrum of microorganisms, especially certain spoilage bacteria.

Accordingly, by application of CuHDO, it is thus now possible to kill, or at least control the growth of microorganisms without using toxic heavy metals such as tin, lead or mercury based compounds.

Thus, CuHDO can be used to preserve process fluids (e.g. water treatment in cooling towers or pulp and paper processing) and to protect goods such as leather, textiles, textile auxiliaries, leather auxiliaries, cosmetics, cleaners, lubricants, metal working fluids, detergents, polymers, plastics, rubber, paper, cardboard, plastics, building materials, cement, tiles, masonry, concrete, pigment preparations, paint formulations, adhesives and sealants against microbial attack. Preferably the CuHDO is used in industrial processes such as cooling towers and pulp and paper processing. Another preferred use of the CuHDO is the in-can preservation of formulated products such as paints and personal care products. Furthermore, as indicated above, surprisingly it was found that CuHDO is very effective in the protection of products, articles and formulations against certain spoilage bacteria, especially *Pseudomonas fluorescens*, *Pseudomonas aeruginosa*, *Alcaligenes faecalis* and *Staphylococcus aureus*, fungi, especially *Aspergillus niger*, *Chaetomium globosum* and *Saccharomyces cerevisiae* and especially the dandruff causing yeast *Malassezia furfur* which makes the use of CuHDO in cosmetics products, another preferred application. The microorganisms mentioned above are ubiquitous in the applications mentioned but normally hard to fight. To date, it was not known that CuHDO is effective against these difficult organisms.

CuHDO may be formulated into a concentrate based either on water or an organic solvent and optionally one or more co-formulants such as emulsifiers or pH-adjusting additives. Preferred formulations are water based and may contain low, more preferably no, volatile organic compounds (VOC). Concentrates of CuHDO may contain between 5 and 60%, more preferably between 10 and 45%, still more preferably between 20 to 40%, especially 20 to 30%, by weight of total concentrate, of CuHDO.

In application, CuHDO is preferably used so as to provide a final concentration from 0.001 to 10%, more preferably 0.01 to 5%, especially 0.02 to 0.5%, by weight of the liquid medium (including any liquid environment to be treated).

In particular, although the pH of the CuHDO concentrate may vary from 2-12, as can that of the medium to be treated, concentrated alkaline formulations are particularly effective against microorganisms. Accordingly, it is preferred that the concentrate and more especially the treated product has a pH of at least 4, more preferably at least 7, still more preferably at least 8, especially 8 to 12.

A preferred product has a pH adjusted to at least 7, more preferably at least 8 using potassium hydroxide. In contrast with most microbicides which can be used at high pH, such as quaternary ammonium compounds, CuHDO does not generate foam and is easy to handle.

CuHDO can be formulated into e.g. pastes, emulsions or solutions or suspension or put onto solid carriers. If required surfactants, emulsifiers, chelants, solubilizers/solvents, salts, corrosion inhibitors, dyes, fragrances, anti-foaming agents or dispersants are included either alone or in combination.

As mentioned above, CuHDO, as a component (A), may be rendered even more effective by combining with another microbicidally effective component (B), as defined above.

In the preferred embodiment of the invention, the CuHDO used is in-situ, i.e. generated directly within the application using a water-soluble salt of N'-hydroxy-N-cyclohexyldiazenium oxide and a Cu-containing salt. Examples of suitable water-soluble salts of N'-hydroxy-N-cyclohexyldiazenium oxide comprise those salts of Group 1 alkali metals e.g. Sodium, Lithium and Potassium, Examples of Cu-containing salts comprise water soluble/dispersible Cu-salts such as Basic Copper Carbonate, Copper Nitrate, Copper Sulphate and Oxides of Copper The in-situ preparation is performed by mixing an aqueous solution of at least one water-soluble salt of N'-hydroxy-N-cyclohexyldiazenium oxide with an aqueous solution/dispersion of at least one Cu-salt.

The in-situ CuHDO is generated within the application by blending copper salts of 1% to 99% Cu content, preferably between 30% to 70%, still more preferably between 40% to 60%, especially 50% to 60%, with a solution of a water soluble salt N'hydroxy-N-cyclo-hexyldiazenium oxide with a concentration of 5% to 95%, more preferably between 10% and 65%, still more preferably between 20% to 40%, especially 30% to 35% by weight of total concentrate of water soluble salt N'hydroxy-N-Cyclohexyldiazenium oxide.

In application, CuHDO is preferably used so as to provide a final concentration of from 0.001% to 10%, more preferably 0.01% to 5%, especially 0.02% to 0.5%, by weight of the liquid medium (including any liquid environment to be treated).

In particular, although the pH of the application medium may vary from 2-12, in-situ CuHDO is particularly effective against microorganisms if the pH of the medium is at least 5, more preferably at least 7, still more preferably at least 8, especially 8 to 12.

Any components (B) or any further additives for the formulation may be added at any time to the solution. They may be added to the combined aqueous solutions after mixing, added in course of mixing or alternatively added to either the solution of the water-soluble salt of N'-hydroxy-N-cyclohexyldiazenium oxide(s) or the solution of the water soluble Cu-salt(s). Preferably the aqueous solvent comprises only water, however it is also possible to some other solvents miscible with water. Examples of such solvents comprise alcohols such as methanol, ethanol, 1-propanol or 2-propanol. In general, the amount of water should be at least 50%, preferably 70% by weight of the total amount of all solvents.

Compositions embodying the invention including such combinations have a particularly strong microbicidal broad spectrum effect and can therefore be used for combating efficiently many undesirable microorganisms. Such combined active components and formulations produced therefrom can act by a chemical route to destroy, discourage or render harmless, harmful organisms, prevent harmful effects or may act in other ways. Formulations embodying the invention may be used to prevent microbial infestation of industrial materials, in other words they can be used for in-can preservation. They serve also as microbicidal finishers of products, in other words they can be used for film conservation.

"Industrial materials" are to be understood as non-living materials, as they are attacked in technical-industrial processes. Industrial materials which can be protected from microbial damage or destruction by formulations embodying the invention are, for example, finishings, drilling oils, dispersions, emulsions, dyes, adhesives, lime, lacquers, pigment preparations, paper, paper processing materials, textiles, textile processing materials, leather, leather processing materials, wood, coating materials, anti-fouling coatings and colours, plastics articles, plastics substrates such as polyethylene, polypropylene, polyamide, polyurethane and the like, cosmetics, washing and cleaning materials, cooling lubricants, hydraulic fluids, joint sealing compounds, window cement, thickening solutions, fleeces as well as carpet layers and other materials which can be attacked or destroyed by microorganisms.

"Industrial processes" are to be understood as installations, especially chemical installations, manufacturing installations or machinery, in which "industrial materials" are used as auxiliaries or reaction media. Examples include reaction vessels, storage vessels, heating vessels (radiators), heat exchanger circuits or air conditioning units.

Likewise, formulations embodying the invention can be used in water treatment. Water treatment is understood as the addition of formulations to processing water, for example, combating slime in the paper industry and for control of harmful organisms in the sugar industry. They prevent or control the growth of microorganisms in cooling circulation systems, air humidification or in drilling and conveying fluid in the oil industry.

Formulations embodying the invention can be used for disinfection of, for example, bottles, instruments, hands, waste, water outflow and in washing. Here, particular examples which can be mentioned are in hospitals, nursing homes and old peoples homes, where disinfection of the above mentioned materials and objects play a particular role, because the patients mostly have the least resistance to infection.

Microorganisms which are capable of infesting and even damaging or destroying industrial materials are bacteria, fungi (e.g. yeasts and moulds) and their spores, algae and slime organisms. Preferably the formulations embodying the invention are effective against bacteria, especially yeasts and moulds as well as algae.

Examples of gram-positive bacteria are Micrococcaceae, Streptococcaceae, Bacilli, Lactobacillaceae, Actinomycetales, especially *Mycobacterium, Dermatophilus*, Nocardiaceae, *Streptomyces* and *Corynebacterium*. Examples of gram-negative microorganisms are Spirochaetales (e.g. Spirochaetaceae and Leptospiraceae), Pseudomonadaceae, Legionellaceae, Neisseriaceae, Enterobacteriaceae, Vibrionaceae, Pasteurellaceae, Bacteroidaceae, Veillonellaceae, Rickettsiaceae, Bartonellaceae and Chlamydiaceae, as well as Brucellaceae.

Examples of yeasts include the families Cryptococcaceae and Sporobolomycetaceae in which are found human pathogenic kinds of *Candida*, Trichospores as well as *Cryptococcus neoformans*. Examples of these are *Candida albicans* and *Saccharomyces cerevisiae*.

An example of a mould within the family zygomycetes is Mucorales; examples of the family Hypomycetes are *Aspergillus* and *Penicillium* and an example of the family Bodariales is *Neurospora*. The representatives of moulds most mentioned are, for example, *Alternaria alternata, Aspergillus niger* and *Penicillium funiculosum*.

Examples of algae include Scenedesmus obliquus, *Euglena gracillis, Chlorella pyrenoidosa, Chlamydomonas pulsatilla, Chlorella salina, Phaeodactylum tricornutum, Chlorella* sp, *Pleurococcus* sp, *Nostoc muscorum, Oscillatoria tenuis, Stichococcus bacillaris* and *Trentepohlia aurea*.

In a composition embodying the invention comprising a combination of (A) and (B), the respective amounts of the components (A) and (B) in the composition are preferably 1 to 99 wt % of (A) and 1 to 99 wt % of (B), more preferably 10 to 90 wt % of (A) and 90 to 10% wt % of (B), especially 40 to 60 wt % of (A) and 40 to 60 wt % of (B).

As in the case of a composition containing CuHDO as the sole microbicidal active component, a composition embodying the invention comprising respective components (A) and (B) may be formulated into a concentrate based either on water or an organic solvent and optionally one or more co-formulants such as emulsifiers or pH-adjusting additives. Again, preferred formulations are water based and may contain low, more preferably no, volatile organic compounds (VOC). The concentrates may contain between 5 and 60%, more preferably between 10 and 45%, still more preferably between 20 to 40%, especially 20 to 30%, by weight of total concentrate, of the combination of respective components (A) and (B).

In application, the combination of active components (A) and (B) is preferably used so as to provide a final concentration of from 0.001 to 10%, more preferably 0.01 to 5%, especially 0.02 to 0.5%, of (A) and (B), by weight of the liquid medium (including any liquid environment to be treated).

In particular, although the pH of the concentrate may vary from 2-12, as can that of the medium to be treated, concentrated alkaline formulations are particularly effective against microorganisms. Accordingly, it is preferred that the concentrate and more especially the treated product has a pH of at least 4, more preferably at least 7, still more preferably at least 8, especially 8-12.

A preferred product has a pH adjusted to at least 7, more preferably at least 8, using a suitable base such as Potassium Hydroxide.

Compositions embodying the invention comprising a combination of components (A) and (B), in dependence upon their chemical and physical properties, can be made up into the usual formulations and preparations as, for example, emulsions, suspensions, dispersions, solutions, powders, pastes or in combination with carrier materials.

To the combinations can optionally be added surface active agents such as surfactants, e.g. emulsifiers, for example, anionic surfactants such as alkylsulfonate and ethersulfate; nonionic surfactants such as fatty alcohol ethoxylate, fatty alcohol esterthiolate, sorbitan ester and polyalkylene glycol; and amphoteric surfactants; chelanats, for example, ethylenediaminetetraacetic acid, nitrilotriacetic acid and methylglycinediacetic acid; solubilizers and/or solvents, for example alcohols such as ethanol, n-propanol and i-propanol, and glycols, for example, propylene glycol and polypropylene glycol, acids and bases, for example, phosphoric acid and caustic soda, inorganic salts and/or other additives, as for example, corrosion inhibitors, anti-foaming agents, dyestuffs and fragrances, either alone or in combination with one another.

It is especially surprising that a composition embodying the invention comprising a combination of (A) CuHDO with (B) another microbicidally effective component can exhibit such a strong effect and indeed, in certain cases, an improved effect against a broad spectrum of microorganisms.

Such strong, or even improved, effects may be observed against, for example, Staphylococcus aureus, *Escherichia coli, Proteus mirabilis, Citrobacter freundii, Pseudomonas fluorescens, Pseudomonas aeruginosa, Alcaligenes faecalis, Candida albicans, Saccharomyces cerevisiae, Alternaria alternata, Aspergillus niger, Penicillium funiculosum* and *Chaetomium globosum*.

For example, a combination of (A) CuHDO and (B) Bronopol has a very strong effect against *Pseudomonas aeruginosa* (PSA), *Candida albicans* (CA), *Proteus mirabilis* (PRM), *Staphylococcus aureus* (STA), *Aspergillus niger* (ASN) and *Escherichia coli* (EC) and exhibits a remarkable improved effect against STA, PRM, PSA and CA.

Indeed, it is particularly advantageous to use this combination against *Pseudomonas aeruginosa* (PSA), which is a pathogenic agent resulting in hospital infections.

Similarly, a combination of (A) CuHDO with (B) 1,2-benzisothiazol-3(2H)-one (BIT) exhibits an excellent improved effect against each of *Pseudomonas aeruginosa, Staphylococcus aureus, Candida albicans* and *Aspergillus niger*.

CuHDO, whether used alone or in combination with other components (B) provides additional performance enhancements in terms of the killing and inhibition of microorganisms. In all tests conducted, equal quantities of in situ generated CuHDO surprisingly outperformed the pre-prepared compound within wet state preservation, across the embodied pH range, as well as dry state film protection.

A further benefit to this aspect of the invention is a reduction in the observed intensity of blue discoloration when producing the compound in situ, making the invention more suitable for use in colour critical applications such as decorative products (e.g. paints and lacquers).

Embodiments of the invention will now be described in more detail with reference to the following Examples.

In can Preservation

Tests were performed according to the IBRG draft method (5.2, June 2001). This briefly entails the substrate being dosed with the biocide and allowed to equilibrate. Samples are inoculated once per week for 4 weeks and checked for recovery of organisms at 1, 3 and 7 days after inoculation.

Results to show efficacy in a polymer based on an acrylic ester and acrylonitrile polymer dispersion using:
1000 ppm CuHDO
1000 ppm in-situ generated CuHDO (by blending within the matrix or medium, 315 ppm of basic copper carbonate containing 57.5% copper content with 3492 ppm of a 30% water soluble solution of potassium salt of N'-hydroxy-N-cyclohexyldiazenium oxide (KHDO))

Using the following performance rating:
P=Pass (0-100 colonies)
F=Fail (101->1000 colonies)

An assessment of the observed intensity of blue discolouration is also included in Table 1 to show further the benefit of the in situ generated invention

TABLE 1

Challenge Test Data for In situ generated CuHDO and Pre-prepared CuHDO

|  | Bacterial Challenges | | | Fungal Challenges | | | Overall Efficacy | | |
| --- | --- | --- | --- | --- | --- | --- | --- | --- | --- |
|  | pH 5 | pH 7 | pH 9 | pH 5 | pH 7 | pH 9 | pH 5 | pH 7 | pH 9 |
| 1000 ppm In situ Generated CuHDO | P | P | P | P | P | P | P | P | P |
| COLOUR | [1]Acceptable very slight blue hue | | | | | | | | |
| 1000 ppm CuHDO Pre-prepared | P | P | P | F[2] | P | P | F[2] | P | P |
| COLOUR | [1]Unacceptable clearly visible blue hue | | | | | | | | |
| Inoculated Control | F | F | F | F | F | F | F | F | F |
| COLOUR | Fully acceptable | | | | | | | | |

P = Pass (0-100 colonies)
F = Fail (101->1000 colonies)
[1]Benefit of invention is a reduction in the observed intensity of the blue discoloration when generating CuHDO in situ, making the invention more suitable for use in colour critical applications such as decorative products (e.g paints and lacquers).
[2]Pre-prepared CuHDO performs well within the embodiment at pH 7-pH 9 whereas in situ generated CuHDO is acceptable over the pH range tested Surface Protection Testing was performed according to the BS3900 G6 and BBA MOAT 33 methods for evaluation versus fungi and algae, respectively. The methods involve painting a substrate panel with the coating and leaching under running water for 72 hours. The substrates are incubated for 56 days after being inoculated with fungi or algae. Performance is judged by comparing with suitable control samples i.e without biocide, a positive control and for fungi with substrate panels that have not been leached.

Performance rating of painted test substrates is as follows and a score of 0, 1 and 2 is considered as a pass
0=no growth
1=trace of growth
2=growth on 1-10% of test face
3=growth on 10-30% of test face
4=growth on 30-70% of test face
5=growth on 70-100% of test face.

Surface Protection using CuHDO

CuHDO was evaluated against a combination product consisting in a paste of N-octyl isothiazolone, Carbendazim and Diuron as well as a reference blank.

TABLE 2

Fungal resistance of coating "as applied".

| | FUNGAL GROWTH ASSESSMENT* | | | | | |
|---|---|---|---|---|---|---|
| | Plaster Substrate | | | Wood Substrate | | |
| TEST SAMPLE (% by weight) | 28 days | 42 days | 56 days | 28 days | 42 days | 56 days |
| 0.15% CuHDO | 1 | 1 | 1 | 1 | 1 | 1 |
| 1.5% CuHDO | 1 | 1 | 1 | 1 | 1 | 1 |
| Blank Control | 5 | 5 | 5 | 5 | 5 | 5 |
| 1.5% Combination Product | 1 | 1 | 1 | 1 | 1 | 2 |

CuHDO concentrations are for the active ingredient.
Combination product concentration is the % use level
Results show the excellent performance of the single active CuHDO versus the combination product and blank.

TABLE 3

Fungal resistance of coating after leaching with running water for 72 hours

| | FUNGAL GROWTH ASSESSMENT* | | | | | |
|---|---|---|---|---|---|---|
| | Plaster Substrate | | | Wood Substrate | | |
| TEST SAMPLE (% by weight) | 28 days | 42 days | 56 days | 28 days | 42 days | 56 days |
| 0.15% CuHDO | 1 | 1 | 2 | 1 | 1 | 2 |
| 1.5% CuHDO | 1 | 1 | 1 | 1 | 1 | 1 |
| Blank Control | 3 | 3 | 4 | 4 | 4 | 4 |
| 1.5% Combination Product | 3 | 3 | 4 | 3 | 4 | 5 |

In this worst case scenario after leaching; the results demonstrate the excellent performance of the single active CuHDO versus the combination product and blank.

TABLE 4

Algal resistance of coatings after leaching with running water for 72 hours

| TEST SAMPLE | ALGAL GROWTH ASSESSMENT* | | |
|---|---|---|---|
| (% by weight) | 28 days | 42 days | 56 days |
| 0.15% CuHDO | 2/2 | 1/1 | 0/1 |
| 1.5% CuHDO | 0/0 | 0/0 | 0/0 |
| Blank Control | 4/4 | 4/4 | 4/5 |
| 1.5% Combination Product | 0/0 | 0/1 | 0/1 |

Results show the excellent performance of the single active CuHDO versus the combination product and blank.

In situ generated Cu-HDO was evaluated against the fungicide IPBC and the algaecide Terbutryn, as well as a reference blank.

Benefit of the invention is a reduction in the observed intensity of the blue discoloration when generating CuHDO in situ, making the invention more suitable for use in colour critical applications e.g. decorative products such as paints and lacquers.

Examples are given below.

TABLE 5

Fungal resistance of coating "as applied".

| | FUNGAL GROWTH ASSESSMENT* | | | | | |
|---|---|---|---|---|---|---|
| | Plaster Substrate | | | Wood Substrate | | |
| TEST SAMPLE (% by weight) | 28 days | 56 days | Colour | 28 days | 56 days | Colour |
| 0.5% In situ CuHDO | 1 | 1 | Fully Acceptable | 1 | 1 | Fully Acceptable |
| 1.0% In situ CuHDO | 1 | 1 | Fully Acceptable | 1 | 1 | Fully Acceptable |
| [3]0.2% CuHDO | 1 | 1 | Unacceptable clearly visible blue hue | 1 | 1 | Unacceptable clearly visible blue hue |
| Blank Control | 3 | 4 | Fully Acceptable | 4 | 5 | Fully Acceptable |
| 0.5% IPBC | 1 | 1 | Fully Acceptable | 1 | 1 | Fully Acceptable |

Results show that no discoloration is observed with the in-situ generated higher concentration CuHDO in contrast to pre-prepared 0.2% CuHDO[3] which exhibits a visible blue hue within the dried coating. The efficacy CuHDO outperforms the blank and is comparable to IPBC.

TABLE 6

Fungal resistance of coating after leaching with running water for 72 hours

| | FUNGAL GROWTH ASSESSMENT* | | | | | |
|---|---|---|---|---|---|---|
| | Plaster Substrate | | | Wood Substrate | | |
| TEST SAMPLE (% by weight) | 28 days | 56 days | Colour | 28 days | 56 days | Colour |
| 0.5% In situ CuHDO | 1 | 1 | Fully Acceptable | 1 | 1 | Fully Acceptable |
| 1.0% In situ CuHDO | 1 | 1 | Fully Acceptable | 1 | 2 | Fully Acceptable |
| ³0.2% CuHDO | 2 | 3 | Unacceptable clearly visible blue hue | 2 | 3 | Unacceptable clearly visible blue hue |
| Blank Control | 4 | 4 | Fully Acceptable | 3 | 5 | Fully Acceptable |
| 0.5% IPBC | 1 | 1 | Fully Acceptable | 1 | 1 | Fully Acceptable |

In this worst case scenario after leaching, CuHDO outperforms the blank and is comparable to IPBC. More surprisingly after leaching the in-situ generated higher concentration CuHDO gives no discoloration in contrast to the pre-prepared 0.2% CuHDO³ which exhibits a visible blue hue within the dried coating

TABLE 7

Algal resistance of coatings after leaching with running water for 72 hours

| TEST SAMPLE | ALGAL GROWTH ASSESSMENT* | | |
|---|---|---|---|
| (% by weight) | 28 days | 56 days | Colour |
| 0.5% In situ CuHDO | 0.0 | 0.0 | Fully Acceptable |
| 1.0% In situ CuHDO | 0.1 | 0.0 | Fully Acceptable |
| ³0.2% CuHDO | 0.1 | 1.2 | Unacceptable clearly visible blue hue |
| Blank Control | 3.3 | 4.4 | Fully Acceptable |
| 0.5% Terbutryn | 0.0 | 0.0 | Fully Acceptable |

In this worst case scenario after leaching, CuHDO outperforms the blank and is comparable to Terbutryn. More surprisingly after leaching the in-situ generated higher concentration CuHDO gives no discoloration in contrast to the pre-prepared 0.2% CuHDO³ which exhibits a visible blue hue within the dried coating

The invention claimed is:

1. A method for combating and/or killing bacteria, mold, yeast and algae in an industrial material, comprising (a) treating an industrial material with an aqueous solution comprising at least one water soluble salt of N'-hydroxy-N-cyclohexyldiazenium oxide, and (b) separately treating the industrial material with an aqueous solution comprising at least one Cu-containing salt, wherein the at least one water soluble salt of N'-hydroxy-N-cyclohexyldiazenium oxide and the Cu-containing salt react in situ to generate a copper salt of N'-hydroxy-N-cyclohexyldiazenium oxide (CuHDO) (component A)) within the industrial material.

2. The method of claim 1, wherein the composition additionally comprises another microbicidally active component (B) selected from: alcohols, isothiazolones, activated halogen compounds, formaldehyde release compounds, phenolic compounds, aldehydes, acids and esters, biphenyls, urea derivatives, O-acetals, O-formals, N-acetals, N-formals, benzamidines, phthalimides, pyridine derivatives, quaternary ammonium and phosphonium compounds, amines, amphoteric compounds, dithiocarbamates, compounds containing active oxygen and mixtures of any of these.

3. The method of claim 2, wherein the another microbicidally active component (B) is selected from at least one of 2-bromo-2-nitropropane-1,3-diol, 1,2-benzisothiazol-3(2H)-one, 1,3,5-tris-(2-hydroxyethyl)-1,3,5-hexahydrotriazine, 5-chloro-2-methyl-2H-isothiazol-3-one, 2-methyl-2H-isothiazol-3-one, tetrahydro-1,3,4,6-tetrakis(hydroxymethyl)-imidazo[4,5-d]imidazole-2,5(2H,3H)-dione, 1,3-dimethyl-5,5-dimethylhydantoin and a polyvinylamine, IPBC, terbutryn, ziram, zineb, dichlofluanid, trichlofuanid, folpet, metal dihexa-2,4-dienoate, tebuconazole, 3-benzo(b)thien-2-yl-5,6-dihydro-1,4,2-oxathiazine-4-oxide, pyrithiones, thiram, cybutryne, MBT, carbendazim, diuron, chlorotoluron, fluorometuron, thiabendazole, metazachlor, CuSCN, or dicopper oxide.

4. The method of claim 3, wherein the respective amounts of the components (A) and (B) in the composition, by weight of the total amount of (A) and (B), are (A) 1 to 99 wt % and (B) 1 to 99 wt %.

5. The method of claim 3, wherein the respective amounts of (A) and (B) are (A) 40 to 60 wt % and (B) 40 to 60 wt %.

6. The method of claim 1, wherein the composition is in the form of a paste, emulsion or solution or suspension.

7. The method of claim 1, wherein the composition has a pH of at least 7.

8. The method of claim 1, wherein the composition has a pH of at least of from 8 to 12.

* * * * *